United States Patent [19]

Krapcho et al.

[11] 4,085,102
[45] Apr. 18, 1978

[54] 2-AMINO-8-ARYLIDENO-3,4,5,6,7,8-HEXAHYDRO-4-ARLYPYRIDO[4,3,d]PYRIMIDINES

[75] Inventors: John Krapcho, Somerset; Chester Frank Turk, Kendall Park, both of N.J.

[73] Assignee: E. R. Squibb & Sons, Inc., Princeton, N.J.

[21] Appl. No.: 817,954

[22] Filed: Jul. 22, 1977

Related U.S. Application Data

[63] Continuation-in-part of Ser. No. 526,754, Nov. 25, 1974, abandoned.

[51] Int. Cl.² .............. C07D 471/04; A61K 31/505
[52] U.S. Cl. ..................... 542/450; 260/256.4 F; 260/256.5 R; 260/293.78; 424/251; 542/435
[58] Field of Search ............ 260/256.4 F, 256.5 R, 260/240 R

[56] References Cited

U.S. PATENT DOCUMENTS

| | | | |
|---|---|---|---|
| 2,517,824 | 8/1950 | Appelquest | 260/256.4 Q |
| 3,186,991 | 6/1965 | Ohnacker | 260/256.4 F |
| 3,248,395 | 4/1966 | Ohnacker | 260/256.4 F |

*Primary Examiner*—Donald G. Daus
*Assistant Examiner*—James H. Turnipseed
*Attorney, Agent, or Firm*—Lawrence S. Levinson; Merle J. Smith; Stephen B. Davis

[57] ABSTRACT

Compounds of the formula

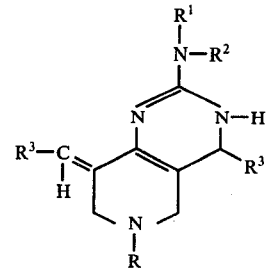

and the pharmaceutically acceptable acid-addition salts thereof wherein $R^1$ and $R^2$ are hydrogen or alkyl of 1 to 4 carbons; R is hydrogen, alkyl of 1 to 4 carbons, alkanoyl of 2 to 5 carbons, or

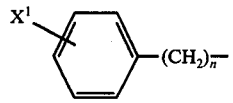

wherein $n$ is 1, 2, or 3; $R^3$ is

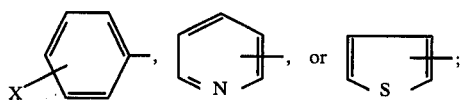

and X and $X^1$ are hydrogen, halogen, alkyl of 1 to 4 carbons, alkoxy of 1 to 4 carbons, or trifluoromethyl are disclosed. These compounds are useful as central nervous system depressants and in particular as muscle relaxants.

7 Claims, No Drawings

2-AMINO-8-ARYLIDENO-3,4,5,6,7,8-HEXAHYDRO-4-ARLYPYRIDO[4,3-d]PYRIMIDINES

This application is a continuation-in-part of Ser. No. 526,754 filed on Nov. 25, 1974 now abandoned.

SUMMARY OF THE INVENTION

This invention relates to new compounds of the formula:

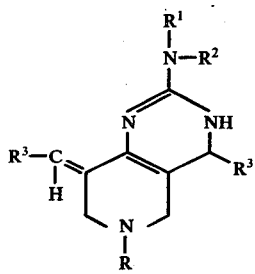

and the pharmaceutically acceptable acid-addition salts thereof which have been found to be useful as central nervous system depressants and in particular as muscle relaxants when administered to mammalian species.

$R^1$ and $R^2$ are independently selected from hydrogen and straight or branched chain alkyl of 1 to 4 carbons. However, when both $R^1$ and $R^2$ are alkyl, the alkyl radicals are straight chain of 1 to 4 carbons.

R is hydrogen, alkyl of 1 to 4 carbons, alkanoyl of 2 to 5 carbons, or

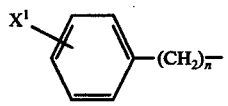

wherein n is 1, 2, or 3.
$R^3$ is selected from

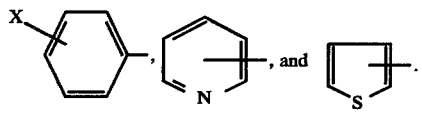

X and $X^1$ are independently selected from hydrogen, halogen, preferably Cl or F, alkyl of 1 to 4 carbons, alkoxy of 1 to 4 carbons, and trifluoromethyl.

The term "alkyl" is intended to include both straight and branched chain radicals, as for example, methyl, ethyl, propyl, isopropyl, butyl, t-butyl, etc. The term "alkoxy" includes such alkyl groups attached to an oxygen atom, i.e. methoxy, ethoxy, propoxy, isopropoxy. The term "alkanoyl" includes such alkyl groups attached to

i.e. acetyl, propionyl, etc.

The term "acid addition salts" is intended to mean salts which may be formed for the purposes of isolation, purification, and storage, such as the oxalate salt, picric salt, etc. and pharmaceutically acceptable salts meant for administration of the compound to a host, such as the hydrochloride, sulfate, acetate, maleate, citrate salts, etc.

DETAILED DESCRIPTION

The new compounds of formula I are prepared by reacting a ketone of formula II wherein R and $R^3$ are as defined above,

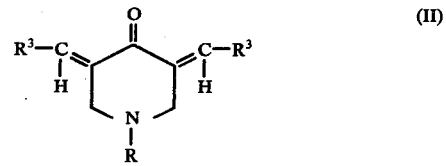

with a compound of formula III, wherein $R^1$ and $R^2$ are as defined above,

The reaction takes place by refluxing the ketone of formula II and the compound of formula III in an aliphatic alkanol solvent of from 1 to 5 carbons, preferably methanol, at a temperature of from about 40° to about 120° C, preferably at about the reflux temperature of the solvent, for from about ½ hour to about 12 hours, preferably for from about 2 to about 6 hours. The compounds of either formula II or III or both may be employed in the form of an acid salt, preferably the hydrochloride salt, in which case sodium methoxide is included within the reaction mixture.

The preparation of the ketones of formula II is disclosed in U.S. patent application Ser. No. 340,408 filed on Mar. 12, 1973, now U.S. Pat. No. 3,852,279.

As disclosed in that application, 1-substituted-4-piperidinone is reacted with an aldehyde of the formula $R^3$—CHO utilizing the reaction procedure described in the Journal of the American Chemical Society, 70, 1824 (1948) to give the compound of formula II wherein R and $R^3$ are as defined above.

The compounds of formula II are generally isolated in the form of their acid addition salts.

Preferred are the compounds of formula I wherein:
$R^1$ and $R^2$ are independently selected from hydrogen, methyl and ethyl, especially wherein $R^1$ and $R^2$ are both hydrogen.

R is hydrogen or alkyl of 1 to 4 carbons, especially hydrogen or methyl.

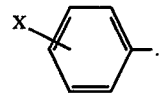

X is hydrogen, Cl, F, $CH_3$, $OCH_3$, or $CF_3$, especially hydrogen or Cl.

The compounds of formula I including the pharmaceutically acceptable acid addition salts thereof have been found to be useful as central nervous system depressants and in particular as muscle relaxants when administered to mammalian species such as rats, dogs, cats, etc., in amounts ranging from about 5 mg. to about 30 mg. per kg. of body weight per day in single or divided doses.

The muscle relaxant property of these compounds is demonstrated by the decrease in limb and abdominal tone observed when the compounds were administered to rats within the above stated dosage range.

For this pharmaceutical purpose a compound or mixture of compounds of formula I or their acid addition salts may be administered orally or parenterally in a conventional dosage form such as tablet, capsule, injectable or the like by compounding with other conventional ingredients such as vehicle, excipient, binder, preservative, flavor, etc., as called for by accepted pharmaceutical practice.

The following examples are illustrative of the invention. All temperatures are expressed on the Centigrade scale.

EXAMPLE 1

3,4,5,6,7,8-Hexahydro-6-methyl-8-(phenylmethylene)-4-phenylpyrido[4,3-d]pyrimidin-2-amine, hydrochloride (1:2)

(a) 1-Methyl-3,5-bis(phenylmethylene)-4-piperidinone, hydrochloride (1:1)

A solution of 57.0 g. (0.5 mole) of 1-methyl-4-piperidinone and 106.0 g. (1.0 mole) of benzaldehyde in 400 ml. of ethanol is cooled in an ice bath and treated with HCl gas until 250 g. is absorbed. The red-colored solution is allowed to stand at room temperature overnight. The resulting deep red-brown solution is seeded, allowed to stand overnight at room temperature, and the crystalline solid is filtered on a sintered-glass funnel and washed with cold ethanol, followed by ether. After drying in a desiccator, the solid (146 g.) is digested in 400 ml. of hot ethanol (75°), cooled and filtered to give 120 g. of pale yellow product, m.p. 242°–244° (dec.).

Recrystallization of 11 g. of this material from 35 ml. of dimethylformamide (DMF) gives 9.2 g. of product, m.p. 242°–244° (dec.).

(b) 3,4,5,6,7,8-Hexahydro-6-methyl-8-(phenylmethylene)-4-phenylpyrido[4,3-d]pyrimidin-2-amine, hydrochloride (1:2)

A stirred suspension of 5 g. (0.015 mole) of 1-methyl-3,5-bis(phenylmethylene)-4-piperidinone, hydrochloride (1:1) from part (a) and 1.6 g. (0.017 mole) of guanidine hydrochloride in 50 ml. of methanol is treated with 1.9 g. (0.035 mole) of sodium methoxide. This mixture is refluxed for 4 hours, cooled, filtered to remove sodium chloride, and the methanol removed on a rotary evaporator to yield 6.3 g. of brittle yellow solid. This material is dissolved in 60 ml. of warm acetonitrile, filtered, cooled and treated with 5 ml. of 6.3 N alcoholic HCl. The dihydrochloride salt separates as a gum which crystallizes after rubbing, warming, and finally cooling overnight to yield 5.2 g. of crude product; m.p. 214°–217° (dec.), s. 196°. Crystallization of 5 g. of this crude product from 15 ml. hot dimethylformamide-45 ml. acetonitrile yields 3.6 g. of pale yellow 3,4,5,6,7,8-hexahydro-6-methyl-8-(phenylmethylene)-4-phenylpyrido[4,3-d]pyrimidin-2-amine, hydrochloride (1:2); m.p. 252–254° (dec.), s. 246°.

EXAMPLE 2

3,4,5,6,7,8-Hexahydro-8-(phenylmethylene)-4-phenylpyrido-[4,3-d]pyrimidin-2-amine, hydrochloride (1:2)

(a) 3,5-Bis(phenylmethylene)-4-piperidinone, hydrochloride (1:1)

A mixture of 14 g. (0.1 mole) of N-acetyl-4-piperidinone and 32 g. (0.3 mole) of benzaldehyde in 150 ml. of ethanol containing 33 ml. of conc. HCl is refluxed for 6 hours and then kept overnight at room temperature. The light yellow solid is filtered, washed with ethanol, washed with ether, and air-dried to yield 26 g. of product; m.p. 273°–275° (dec.).

(b) 3,4,5,6,7,8-Hexahydro-8-(phenylmethylene)-4-phenylpyrido-[4,3-d]pyrimidin-2-amine, hydrochloride (1:2)

A stirred suspension of 11 g. (0.035 mole) of 3,5-bis(phenylmethylene)-4-piperidinone, hydrochloride (1:1) from part (a) and 3.8 g. (0.04 mole) of guanidine hydrochloride in 200 ml. of ethanol is treated with 4.4 g. (0.082 mole) of sodium methoxide. This mixture is refluxed for 4 hours, allowed to stand overnight at room temperature, filtered to remove sodium chloride, and the ethanol removed on a rotary evaporator to give 11.6 g. of light yellow solid; m.p. 132°–134° (foam), s. 126°. This material is dissolved in 100 ml. of methanol and 50 ml. of CHCl₃, cooled, treated with 12 ml. of 6.2 N alcoholic HCl, and the solvents evaporated to give 12.8 g. of a brittle yellow solid having an indefinite melting point. Crystallization from 150 ml. of isopropanol yields 7.5 g. of yellow solid 3,4,5,6,7,8-hexahydro-8-(phenylmethylene)-4-phenylpyrido[4,3-d]pyrimidin-2-amine, hydrochloride (1:2); m.p. 235°–237° (dec.), s. 215°.

EXAMPLE 3

4-(4-Chlorophenyl)-8-[(4-chlorophenyl)methylene]-3,4,5,6,7,8-hexahydro-6-methylpyrido[4,3-d]pyrimidin-2-amine, hydrochloride (1:2)

(a) 3,5-Bis[(4-chlorophenyl)methylene]-1-methyl-4-piperidinone, hydrochloride (1:1)

22.6 g. (0.2 mole) of 1-methyl-4-piperidinone and 85 g. (0.6 mole) of p-chlorobenzaldehyde are reacted in 300 ml. of ethanol in the presence of 66 ml. of conc. HCl to give 19 g. of crude product; m.p. 253°–255°. Crystallization from 120 ml. of hot dimethylformamide and 240 ml. of acetonitrile yields 13.7 g. of yellow solid 3,5-bis[(4-chlorophenyl)-methylene]-1-methyl-4-piperidinone, hydrochloride (1:1); m.p. 256°–258°.

(b) 4-(4-Chlorophenyl)-8-[(4-chlorophenyl)methylene]-3,4,5,-6,7,8-hexahydro-6-methylpyrido[4,3-d]pyrimidin-2-amine, hydrochloride (1:2)

A stirred suspension of 4.4 g. (0.011 mole) of 3,5-bis[(4-chlorophenyl)methylene]-1-methyl-4-piperidinone, hydrochloride (1:1) from part (a) and 1.2 g. (0.012 mole) of guanidine hydrochloride in 50 ml. of methanol is treated with 1.4 g. (0.026 mole) of sodium methoxide. This mixture is refluxed for 4 hours, cooled, filtered to remove sodium chloride, and the methanol removed on a rotary evaporator to yield 6.4 g. of a yellow tacky residue. This material is dissolved in 50 ml. of warm acetonitrile, filtered, cooled, treated with 4 ml. of 6.0 N alcoholic HCl, and diluted with 150 ml. of ethyl acetate to precipitate 4.5 g. of the yellow solid dihydrochloride salt; m.p. 225°–227° (dec.). Crystallization from 15 ml. hot dimethylformamide-45 ml. of acetonitrile yields 3.0 g. of cream-colored solid 4-(4-chlorophenyl)-8-[(4-chlorophenyl)methylene]-3,4,5,6,7,8-hexahydro-6-methylpyrido[4,3-d]pyrimidin-2-amine, hydrochloride (1:2); m.p. 236°–238° (dec.), s. 231°.

EXAMPLE 4

4-(2-Chlorophenyl)-8-[(2-chlorophenyl)methylene]-3,4,5,6,7,8-hexahydro-6-methylpyrido[4,3-d]pyrimidin-2-amine, hydrochloride (1:2)

(a) 3,5-Bis[(2-chlorophenyl)methylene]-1-methyl-4-piperidinone

A stirred solution of 11.3 g. (0.1 mole) of 1-methyl-4-piperidinone and 28 g. (0.2 mole) of o-chlorobenzaldehyde in 220 ml. of ethanol is treated with 11 g. (0.17 mole) of 85% KOH. The temperature rises to 34° and after approximately 2 minutes a solid begins to separate. After stirring for 30 minutes the yellow solid is filtered, washed with water, and air-dried to yield 31.6 g. of yellow, 3,5-bis[(2-chlorophenyl)methylene]-1-methyl-piperidinone; m.p. 148°–150°.

(b) 4-(2-Chlorophenyl)-8-[(2-chlorophenyl)methylene]-3,4,5,-6,7,8-hexahydro-6-methylpyrido[4,3-d]pyrimidin-2-amine, hydrochloride (1:2)

A stirred suspension of 14.3 g. (0.04 mole) of 3,5-bis[(2-chlorophenyl)methylene]-1-methyl-4-piperidinone from part (a) and 4.3 g. (0.045 mole) of guanidine hydrochloride in 150 ml. of methanol is treated with 2.5 g. (0.046 mole) of sodium methoxide. This mixture is refluxed for 4 hours, cooled, filtered to remove sodium chloride, and the methanol removed on a rotary evaporator to yield 22 g. of a light yellow solid; m.p. 95°–97° (foaming). This material is crystallized from a mixture of 150 ml. of benzene and 300 ml. of hexane to give 13.6 g. of light yellow 4-(2-chlorophenyl)-8-[(2-chlorophenyl)methylene]-3,4,5,6,7,8-hexahydro-6-methyl-pyrido[4,3-d]pyrimidin-2-amine; m.p. 118°–120°.

This base is suspended in 150 ml. of acetonitrile, stirred, cooled and treated with 12 ml. of 6.0 N alcoholic HCl to form a light colored solid. After diluting with ether and cooling overnight, the material is filtered, washed with ether, and dried in vacuo to yield 14.5 g. of pale yellow solid; m.p. 301°–303° (dec.). Digestion with 75 ml. of warm dimethylsulfoxide and 150 ml. acetonitrile, yields 12.8 g. of colorless 4-(2-chlorophenyl)-8-[(2-chlorophenyl)methylene]-3,4,5,6,7,8-hexahydro-6-methylpyrido[4,3-d]-pyrimidin-2-amine, hydrochloride (1:2); m.p. 307°–309° (dec.).

EXAMPLES 5–22

Following the procedure of example 1 but substituting for the 1-methyl-3,5-bis(phenylmethylene)-4-piperidinone in part (b) the compounds shown below in Col. A one obtains the products shown in Col. B.

| Ex. | R | R³ |
|---|---|---|
| 5 | —C₂H₅ | phenyl |
| 6 | —i-C₃H₇ | 4-methylphenyl |
| 7 | —t-C₄H₉ | 2-methoxyphenyl |
| 8 | —n-C₄H₉ | 4-trifluoromethylphenyl |
| 9 | —H | 3-pyridyl |
| 10 | —CH₃ | 4-pyridyl |

-continued

| | Col. A | Col. B | |
|---|---|---|---|
| Ex. | R | | R³ |
| 11 | —CH₃ | | 2-thienyl |
| 12 | —CH₂—C₆H₅ | | phenyl |
| 13 | —CH₂—C₆H₄—F (4-) | | phenyl |
| 14 | —CH₂—C₆H₄—Cl (2-) | | C₆H₄—F (4-) |
| 15 | —(CH₂)₂—C₆H₅ | | phenyl |
| 16 | —(CH₂)₃—C₆H₅ | | phenyl |
| 17 | —C(O)—CH₃ | | C₆H₄—Cl (4-) |
| 18 | —C(O)—C₂H₅ | | phenyl |
| 19 | —CH₃ | | C₆H₄—Cl (2-) |
| 20 | —C₂H₅ | | C₆H₄—CH₃ (3-) |
| 21 | —H | | 2-pyridyl |

-continued

| Col. A | Col. B |
|---|---|
| 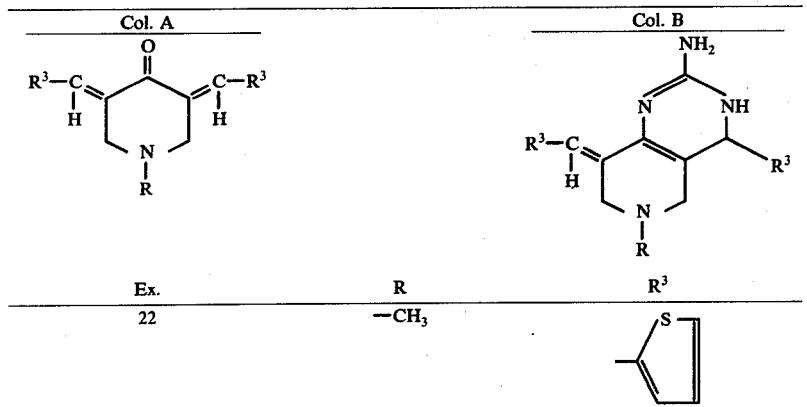 | |

| Ex. | R | R³ |
|---|---|---|
| 22 | —CH₃ | (thienyl) |

EXAMPLES 23–36

Following the procedure of example 1 but employing in part (b) the substituted guanidines shown below in Col. A one obtains the products shown in Col. B.

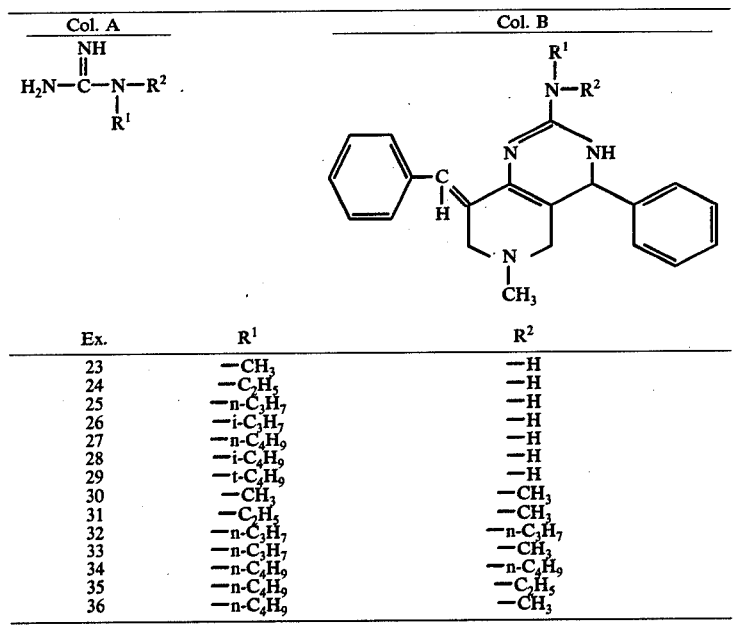

| Ex. | R¹ | R² |
|---|---|---|
| 23 | —CH₃ | —H |
| 24 | —C₂H₅ | —H |
| 25 | —n-C₃H₇ | —H |
| 26 | —i-C₃H₇ | —H |
| 27 | —n-C₄H₉ | —H |
| 28 | —i-C₄H₉ | —H |
| 29 | —t-C₄H₉ | —H |
| 30 | —CH₃ | —CH₃ |
| 31 | —C₂H₅ | —CH₃ |
| 32 | —n-C₃H₇ | —n-C₃H₇ |
| 33 | —n-C₃H₇ | —CH₃ |
| 34 | —n-C₄H₉ | —n-C₄H₉ |
| 35 | —n-C₄H₉ | —C₂H₅ |
| 36 | —n-C₄H₉ | —CH₃ |

Similarly, by employing the substituted guanidines of examples 23 to 36 in the procedures of examples 2 to 22, other compounds within the scope of the invention are obtained.

What is claimed is:

1. A compound of the formula:

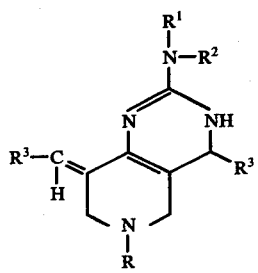

wherein R is selected from the group consisting of hydrogen, alkyl of 1 to 4 carbons,

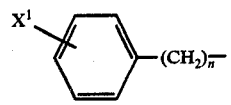

wherein $n$ is 1, 2, or 3, and alkanoyl of 2 to 5 carbons; R¹ and R² are independently selected from the group consisting of hydrogen and straight or branched chain alkyl of 1 to 4 carbons provided that wherein R¹ and R² are both alkyl, the alkyl chains are straight of 1 to 4 carbons; R³ is selected from the group consisting of

pyridyl, and thienyl; and X and X¹ are independently selected from the group consisting of hydrogen, halogen, alkyl of 1 to 4 carbons, alkoxy of 1 to 4 carbons, and trifluoromethyl; and the pharmaceutically acceptable acid addition salts thereof.

2. The compound of claim 1 wherein R is hydrogen or alkyl of 1 to 4 carbons; $R^1$ and $R^2$ are independently selected from the group consisting of hydrogen, methyl, and ethyl; and $R^3$ is

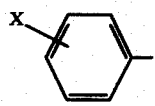

wherein X is hydrogen, Cl, F, $OCH_3$, $CH_3$, or $CF_3$.

3. The compound of claim 2 wherein R is hydrogen or methyl; $R^1$ and $R^2$ are both hydrogen; and X is hydrogen or Cl.

4. The compound of claim 3 having the name 3,4,5,6,7,8-hexahydro-6-methyl-8-(phenylmethylene)-4-phenylpyrido[4,3-d]pyrimidin-2-amine, hydrochloride (1:2).

5. The compound of claim 3 having the name 3,4,5,6,7,8-hexahydro-8-(phenylmethylene)-4-phenylpyrido[4,3-d]pyrimidin-2-amine, hydrochloride (1:2).

6. The compound of claim 3 having the name 4-(2-chlorophenyl)-8-[(2-chlorophenyl)methylene]-3,4,5,6,7,8-hexahydro-6-methylpyrido[4,3-d]pyrimidin-2-amine, hydrochloride (1:2).

7. The compound of claim 3 having the name 4-(4-chlorophenyl)-8-[(4-chlorophenyl)methylene]-3,4,5,6,7,8-hexahydro-6-methylpyrido[4,3-d]pyrimidin-2-amine, hydrochloride (1:2).

* * * * *

UNITED STATES PATENT AND TRADEMARK OFFICE
CERTIFICATE OF CORRECTION

PATENT NO. : 4,085,102
DATED : April 18, 1978
INVENTOR(S) : John Krapcho et al.

It is certified that error appears in the above-identified patent and that said Letters Patent are hereby corrected as shown below:

In the title, second line, "AHYDRO-4-ARLYPYRIDO[4,3,d]PYRIMI- should read -- AHYDRO-4-ARYLPYRIDO[4,3-d]PYRIMI- --.

Col. 1, in the title, second line "DRO-4-ARLYPYRIDO[4,3-d] PYRIMIDINES" should read -- DRO-4-ARYLPYRIDO[4,3-d]PYRIMIDINES- --.

Col. 2, line 55 should read -- $R^3$ is  -- .

Following the compound in Claim 1, insert -- wherein R is selected from the group consisting of hydrogen, alkyl of 1 to 4 carbons, -- .

Signed and Sealed this

Thirty-first Day of October 1978

[SEAL]

Attest:

RUTH C. MASON
Attesting Officer

DONALD W. BANNER
Commissioner of Patents and Trademarks